(12) United States Patent
Hodges et al.

(10) Patent No.: US 6,946,067 B2
(45) Date of Patent: Sep. 20, 2005

(54) METHOD OF FORMING AN ELECTRICAL CONNECTION BETWEEN AN ELECTROCHEMICAL CELL AND A METER

(75) Inventors: Alastair McIndoc Hodges, Blackburn South (AU); Garry Chambers, Vermont (AU)

(73) Assignee: LifeScan, Inc., Milpitas, CA (US)

( * ) Notice: Subject to any disclaimer, the term of this patent is extended or adjusted under 35 U.S.C. 154(b) by 265 days.

(21) Appl. No.: 10/317,036

(22) Filed: Dec. 9, 2002

(65) Prior Publication Data

US 2003/0217934 A1 Nov. 27, 2003

Related U.S. Application Data

(60) Provisional application No. 60/345,743, filed on Jan. 4, 2002.

(51) Int. Cl.[7] .............. G01F 1/64; G01N 27/26; G01N 1/00
(52) U.S. Cl. .......... 205/792; 205/775; 204/401; 204/403.01; 204/403.02; 204/403.11
(58) Field of Search .............. 205/775, 792, 205/794.5; 204/401, 403.01, 403.11, 400, 403.02, 406, 407, 280, 281, 290.01; 29/592; 174/68.1; 429/92, 93, 144, 147

(56) References Cited

U.S. PATENT DOCUMENTS

| | | | |
|---|---|---|---|
| 5,437,999 A | | 8/1995 | Diebold et al. |
| 5,502,396 A | | 3/1996 | Desarzens et al. |
| 6,001,239 A | * | 12/1999 | Douglas et al. ............. 205/778 |
| 6,113,762 A | | 9/2000 | Karube et al. |
| 6,174,420 B1 | | 1/2001 | Beck et al. |
| 6,179,979 B1 | | 1/2001 | Beck et al. |
| 6,258,229 B1 | | 7/2001 | Winarta et al. |
| 6,558,528 B1 | * | 5/2003 | Matzinger ................. 205/777.5 |
| 6,743,635 B2 | * | 6/2004 | Neel et al. .................... 436/95 |
| 2002/0168290 A1 | * | 11/2002 | Yuzhakov et al. ............ 422/56 |
| 2003/0217934 A1 | | 11/2003 | Hodges et al. |

FOREIGN PATENT DOCUMENTS

| | | |
|---|---|---|
| EP | 0 964 059 | 12/1999 |
| WO | WO 98/43073 | 10/1998 |
| WO | WO 98/43074 | 10/1998 |
| WO | WO 00/20626 | 4/2000 |
| WO | WO 01/057238 | 8/2001 |

* cited by examiner

Primary Examiner—Nam Nguyen
Assistant Examiner—R. Michelle Vestal
(74) Attorney, Agent, or Firm—Nutter McClennen & Fish, LLP

(57) ABSTRACT

A method of forming an electrical connection between an electrochemical cell and a meter is provided. According to the method, an electrical connection is made between a meter, by means of a wedge-shaped connector with upper and lower conductive surfaces, and an electrochemical cell comprising a first substrate with a first electrically conductive coating and a second substrate with a second electrically conductive coating, the electrically conductive coatings being disposed to face each other in a spaced apart relationship by an insulating spacer. The meter further includes a pivot point for rotating the wedge connector on the pivot point.

2 Claims, 6 Drawing Sheets

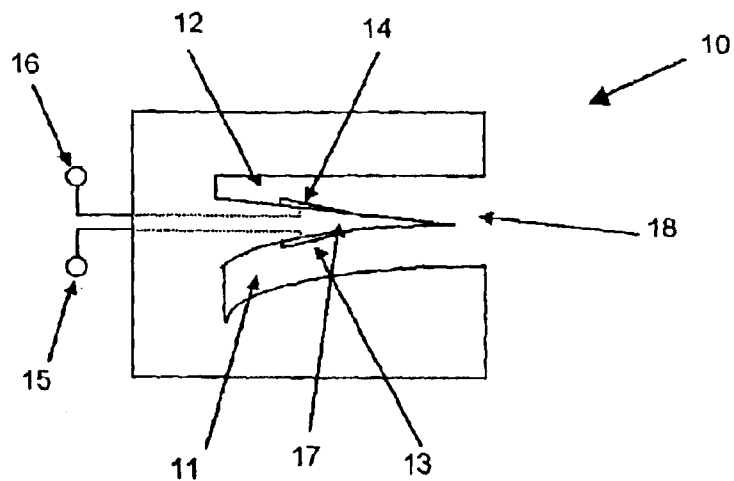
Figure 7.
Figure 8.
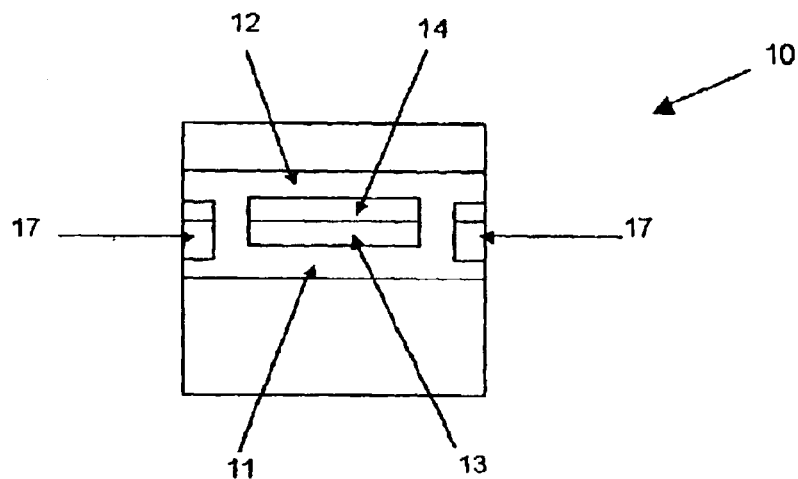
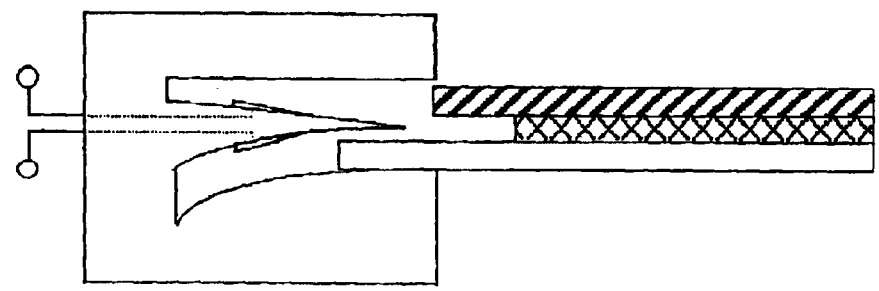
Figure 9.

METHOD OF FORMING AN ELECTRICAL CONNECTION BETWEEN AN ELECTROCHEMICAL CELL AND A METER

RELATED APPLICATION

This application claims the benefit of U.S. Provisional Application No. 60/345,743, filed Jan. 4, 2002.

FIELD OF THE INVENTION

The present invention relates to electrochemical cells including a connector which mates with a meter connection device to provide electrical connection to meter circuitry.

BACKGROUND OF THE INVENTION

Miniature electrochemical cells are useful in applications such as chemical sensing wherein the electrodes of a strip element interface with an electronic device. The electronic device, often termed a meter, measures the electrical response of the strip element to the sample and can also supply power to the strip element to perform a test. In order to perform these functions, the strip element electrodes must be able to make electrical connection to the meter circuitry. Such an electrical connection may be made via a connection device on the meter which mates with areas on the strip element in electrical communication with the electrochemical cell electrodes.

In configurations of electrochemical cells as disclosed in WO 98/43073, U.S. Pat. No. 5,437,999, EP 0 964 059 A2, WO 00/20626, an upper and a lower electrode face oppose one another with an electrically insulating layer between them. The electrodes in such a configuration are typically formed on separate substrates that are assembled during manufacture of the electrochemical cell. This configuration presents difficulties in manufacture when forming a part by which the strip element electrodes are connected to the meter circuitry, as it is different from the usual connection configuration where the connection areas are all on the same plane.

The issue of connection areas in different planes has been addressed in various ways. In WO 98/43073, a method and device are disclosed wherein cut-outs are formed in one of the electrode layers and in the insulating layer to expose an area of the underlying electrode layer which can be used as an connection area. In U.S. Pat. No. 5,437,999 and WO 00/20626, a method an device are disclosed wherein a flap is formed on one electrode layer with a corresponding cut-out in the other electrode layer to expose a suitable connection area. In this configuration, the insulating layer is cut short so as not interfere with the connection area.

In EP 0 964 059 A2, the insulating layer is cut short, and a hole is formed in the upper substrate in order to expose a connection area at the base of the well that is formed. The well may be filled with a conductive material and a contact made with the conductive material at the top of the filled well, thus bringing the connection areas onto one plane.

A drawback to these configurations is that they require features on more than one of the cell layers to be in registration with one another when the layers are assembled into a working device. This creates difficulties in manufacturing the devices and limits the manufacturing techniques that can be used. In particular, for costs and throughput considerations, it is often desirable to manufacture the strip elements in a continuous web form. When using continuous webs it is often difficult to reliably achieve the down-web registration of repeating features formed on different layers prior to a lamination step. Often this requires expensive control systems and a relatively fragile fabrication process, if it is possible at all.

SUMMARY OF THE INVENTION

Electrochemical cell connectors that are suitable for use in conjunction with opposing electrode electrochemical cells, and methods of forming them, that require no down-web registration steps prior to lamination of the layers are desirable. The preferred embodiments provide such electrochemical cell connectors and methods.

In a first embodiment, an electrochemical cell is provided, the electrochemical cell adapted for electrical connection with a meter, the cell including a first insulating substrate carrying a first electrically conductive coating, a second insulating substrate carrying a second electrically conductive coating, and an insulating spacer layer disposed therebetween, the electrically conductive coatings being disposed to face each other in a spaced apart relationship, wherein an edge of the first insulating substrate carrying the first electrically conductive coating extends beyond an edge of the second insulating substrate carrying the second electrically conductive coating and beyond an edge of the insulating spacer layer, and wherein the edge of the second insulating substrate carrying the second electrically conductive coating extends beyond the edge of the insulating spacer layer.

In an aspect of the first embodiment, the first insulating substrate carrying the first electrically conductive coating includes an aperture in a portion of the first insulating substrate carrying the first electrically conductive coating that extends beyond the edge of the insulating spacer, such that an area of the second electrode layer is exposed so as to provide a surface for forming an electrical connection with a meter via the aperture.

In an aspect of the first embodiment, the cell further includes an additional insulating spacer layer, the additional spacer layer disposed between the first electrically conductive coating and the second electrically conductive coating, wherein the insulating spacer layer and the additional spacer layer are situated on opposite sides of the aperture.

In a second embodiment, an electrochemical cell is provided, the electrochemical cell adapted for electrical connection with a meter, the cell including a first insulating substrate carrying a first electrically conductive coating, a second insulating substrate carrying a second electrically conductive coating, and an insulating spacer layer disposed therebetween, the electrically conductive coatings being disposed to face each other in a spaced apart relationship, wherein an edge of the first insulating substrate carrying the first electrically conductive coating extends beyond an edge of the second insulating substrate carrying the second electrically conductive coating and beyond an edge of the insulating spacer layer, and wherein the first insulating substrate carrying the first electrically conductive coating and the insulating spacer layer include an aperture, such that an area of the second electrode layer is exposed so as to provide a surface for forming an electrical connection with a meter via the aperture.

In a third embodiment, an electrochemical cell is provided, the electrochemical cell adapted for electrical connection with a meter, the cell including a first insulating substrate carrying a first electrically conductive coating, a second insulating substrate carrying a second electrically conductive coating, and an insulating spacer layer disposed therebetween, the electrically conductive coatings being disposed to face each other in a spaced apart relationship, wherein a portion of the first insulating substrate carrying the first electrically conductive coating extends beyond an edge of the second insulating substrate carrying the second electrically conductive coating and beyond an edge of the insulating spacer layer, and wherein a portion of the first insulating substrate carrying the first electrically conductive coating and a portion of the insulating spacer are removed so as to form a notch, the notch situated adjacent to the edge of the second insulating substrate carrying the second electrically conductive coating and the edge of the insulating spacer layer, such that an area of the second electrode layer is exposed so as to provide a surface for forming an electrical connection with a meter.

In a fourth embodiment, a method for forming an electrical connection between an electrochemical cell and a meter is provided, the method including the steps of: providing an electrochemical cell, the electrochemical cell comprising a first insulating substrate carrying a first electrically conductive coating, a second insulating substrate carrying a second electrically conductive coating, and an insulating spacer layer disposed therebetween, the electrically conductive coatings being disposed to face each other in a spaced apart relationship, wherein an edge of the first insulating substrate carrying the first electrically conductive coating extends beyond an edge of the second insulating substrate carrying the second electrically conductive coating and beyond an edge of the insulating spacer layer, and wherein the edge of the second insulating substrate carrying the second electrically conductive coating extends beyond the edge of the insulating spacer layer; providing a meter, the meter including a wedge, the wedge including an upper wedge conductive surface and a lower wedge conductive surface, the conductive surfaces in electrical communication with the meter; and inserting a portion of the electrochemical cell into the meter, whereby the wedge is inserted between the portion of the first insulating substrate carrying the first electrically conductive coating and the portion of the second insulating substrate carrying the second electrically conductive coating that extends beyond the edge of the insulating spacer layer, whereby an electrical connection between the first electrically conductive coating and the lower wedge conductive surface is formed, and whereby an electrical connection between the second electrically conductive coating and the upper wedge conductive surface is formed.

In an aspect of the fourth embodiment, the meter further includes a pivot point, wherein the wedge is capable of rotating on the pivot point.

BRIEF DESCRIPTION OF THE DRAWINGS

FIG. 1a illustrates a top view and FIG. 1b a cross-section view.

FIG. 2a illustrates a top view and FIG. 2b a cross-section view.

FIG. 3a illustrates a top view and FIG. 3b a cross-section view.

FIG. 4a illustrates a top view and FIG. 4b a cross-section view.

FIG. 5a illustrates a top view and FIG. 5b a cross-section view.

FIG. 6a illustrates a top view and FIG. 6b a cross-section view.

FIG. 7 provides a side view illustrating the splitting of element 1 from element 2 in the connector area to allow access for a tongue connection device.

FIG. 8 provides an end view illustrating the splitting of element 1 from element 2 in the connector area to allow access for a tongue connection device.

FIG. 9 provides an illustration depicting a strip partially inserted into an external circuit connector.

DETAILED DESCRIPTION OF THE PREFERRED EMBODIMENT

Figure 1A:
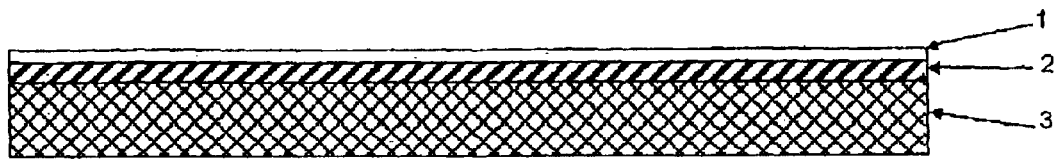
FIGS. 1a and 1b provide schematics of an electrochemical cell wherein element 2 is offset from the corresponding edge of element 1 so as to expose the conductive coating on element 1.
Figure 1B:
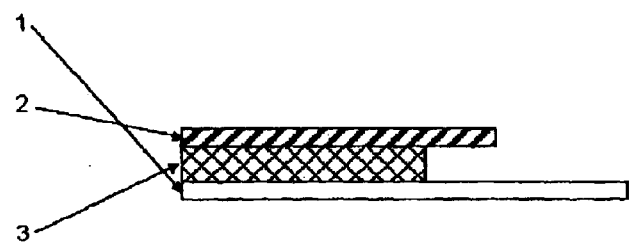
Figure 2A:
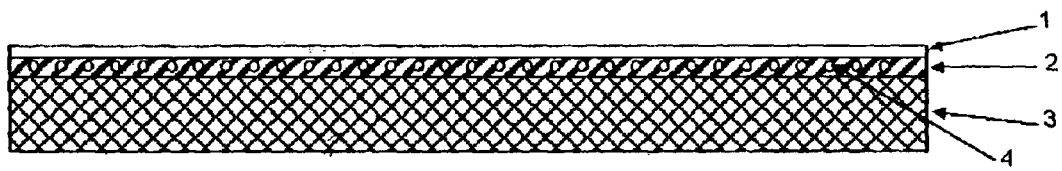
FIGS. 2a and 2b provide schematics of an electrochemical cell wherein a through hole is cut in element 1 to expose the conductive coating on element 2 for electrical connection.
Figure 2B:
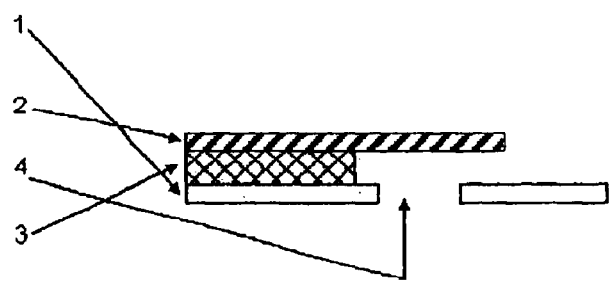
Figure 3A:
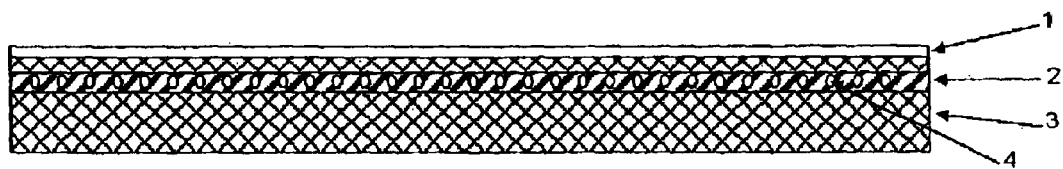
FIGS. 3a and 3b provide schematics of an electrochemical cell similar to the cell of FIG. 2, except that an extra portion of element 3 has been inserted between elements 1 and 2.
Figure 3B:
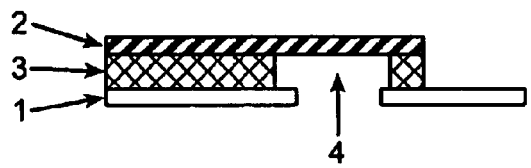
Figure 4A:
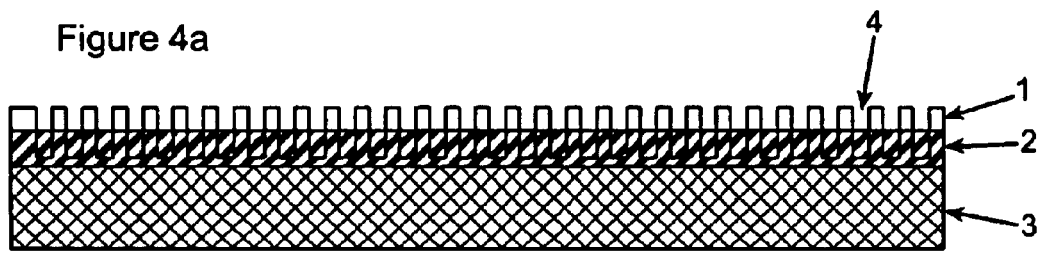
FIGS. 4a and 4b provide schematics of an electrochemical cell wherein a slot is formed in element 1, which gives access to an area of the conductive coating on element 2.
Figure 4B:
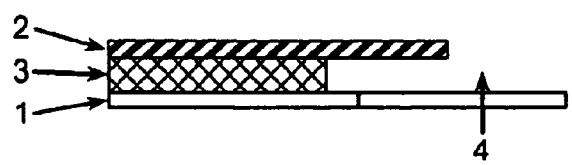
Figure 5A:
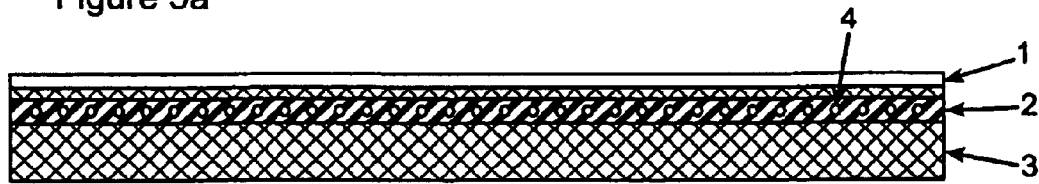
FIGS. 5a and 5b provide schematics of an electrochemical cell similar to the cell of FIG. 2, except that the edge of element 3 is such that it is situated above element 4 in element 1.
Figure 5B:
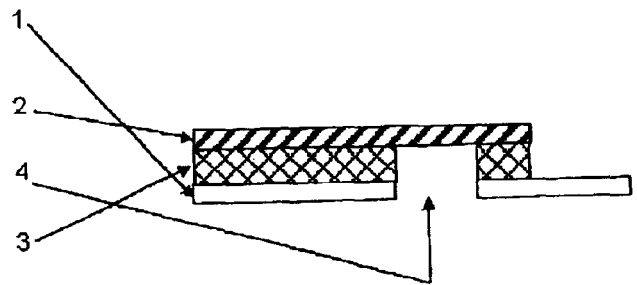
Figure 6A:
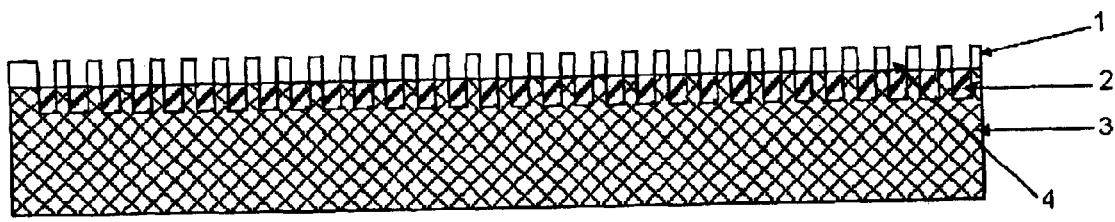
FIGS. 6a and 6b provide schematics of an electrochemical cell similar to the cell of FIG. 4, except that the edge of element 3 is such that it is at least close to the edge of element 1.
Figure 6B:
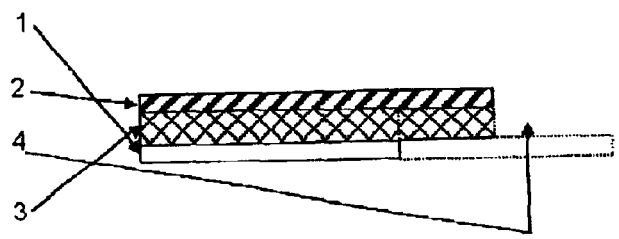

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The preferred embodiments relate to devices and methods for forming electrode connection areas in electrochemical cells with opposing electrodes. The devices and methods do not require the registration of features formed on different layers prior to the lamination of the layers. In particular, devices and methods that do not require the down-web registration of repeating features on different layers during lamination of continuous webs of devices during manufacture are provided. The preferred embodiments may be used in conjunction with any suitable fabrication process, for example, a process wherein discrete sections of the layers are laminated together and wherein it is advantageous to lessen the registration requirements and therefore the manufacturing complexity.

In another embodiment, preferred elements of the port in a meter device suitable for use with the disclosed strip connectors are provided.

The basic feature of the electrochemical cells illustrated in FIGS. 1–6 is that the edge of at least one electrode layer (herein termed the upper electrode layer) is offset from at least one other opposing electrode layer (here termed the lower electrode layer) such that an area of the lower electrode layer overhangs the edge of the upper electrode layer, thus exposing an area of the lower electrode layer suitable for connection to meter circuitry.

FIGS. 1 to 6 depict views of various preferred embodiments of electrochemical cell connectors. FIGS. 1a, 2a, 3a, 4a, 5a, and 6a depict top views of sections of web or card of the assembled layers for various embodiments, showing the repeating features. FIGS. 1b, 2b, 3b, 4b, 5b, and 6b depict the corresponding cross-sectional views.

In FIGS. 1 to 6, element 1 is the lower electrode layer. This layer consists of an electrically insulating substrate with an electrically conductive coating applied to its upper face, wherein the electrically conductive coating is in electrical contact with at least a first electrode of the electrochemical cell.

Element 2 is the upper electrode layer. This layer consists of an electrically insulating substrate with an electrically conductive coating applied to its lower face, wherein the electrically conductive coating is in electrical contact with at least a second electrode of the electrochemical cell.

Element 3 is an electrically insulating layer which serves to space elements 1 and 2 apart. In preferred embodiments, the upper and lower faces of element 3 are adhesive and also serve to adhere the layers of the device together. In this preferred embodiment, element 3 may consist of a substrate coated with an adhesive. Alternatively it may consist of just an adhesive layer.

Element 4 is a cut-out feature in element 1 which, as illustrated in FIGS. 2 to 6, serves to give access to an exposed area of the electrically conductive coating on the lower face of element 2.

In FIG. 1, one edge of element 2 is offset from the corresponding edge of element 1, such that an overhanging area of the conductive coating on element 1 is exposed. In a preferred embodiment, a tongue of electrically insulating substrate material with electrically conductive coatings or layers on its upper and lower faces is inserted between elements 1 and 2 to make electrical connection to the meter circuitry.

In FIG. 2, a through hole is cut in element 1 to expose an area of the conductive coating on element 2 for electrical connection. This obviates the need for having a connection device inserted between the layers.

The device depicted in FIG. 3 is similar to that depicted in FIG. 2, except that an extra portion of element 3 has been inserted between elements 1 and 2. This configuration is desirable if it is likely that elements 1 and 2 will be pushed together during use and thus create an electrical short-circuit between the conductive coatings on elements 1 and 2.

FIG. 4 depicts an embodiment where a slot has been formed in element 1 which gives access to an area of the conductive coating on element 2.

FIG. 5 depicts a similar embodiment to FIG. 2. However in this embodiment the edge of element 3 is such that it is above element 4 in element 1. In order for this embodiment to be operable in the preferred embodiment elements 1 and 2 must be laminated or otherwise assembled together before element 4 is formed.

FIG. 6 depicts a similar embodiment to FIG. 4. However in this embodiment the edge of element 3 is such that it is at least close to the edge of element 1. In this embodiment, it is preferred that elements 1 and 2 be laminated or otherwise assembled together before element 4 is formed.

In another embodiment, methods are disclosed for forming electrical connections to some of the connection devices discussed above.

For the electrochemical cells of the preferred embodiments depicted in FIGS. 2 to 6, it is suitable to use parts for the connection of the conductive coatings on elements 1 and 2 to external circuitry such as those described in U.S. Pat. No. 6,379,513.

For the embodiment depicted in FIG. 1, a different configuration for external connection is desirable. For this embodiment, it is desirable to split element 1 from element 2 in the connector area to allow easier access for a tongue connection device. According to this aspect of the embodiment, element 1 is split from element 2 during insertion of the strip connector into external circuitry connector, e.g., by a blade or wedge-shaped projection, or other suitable splitting device.

Figure 10:
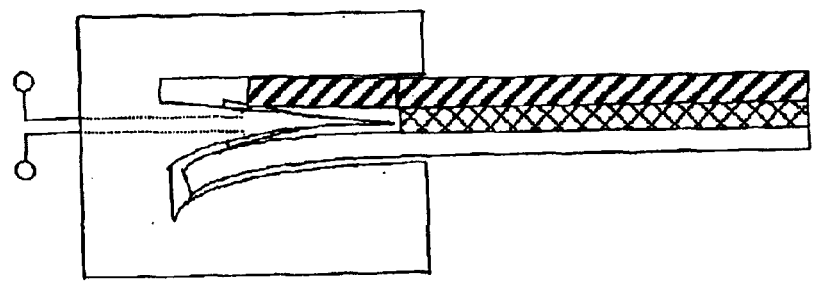
FIG. 10 provides an illustration depicting a strip fully inserted into an external circuit connector.

FIGS. 7 and 8 show a side view and end view, respectively, that illustrate the splitting of element 1 from element 2 in the connector area to allow access for a tongue connection device. FIGS. 9 and 10 show this embodiment with a strip partially and fully inserted, respectively, into the external circuit connector.

The external circuit connector 10, depicted in FIGS. 7 to 10, contains a chamber 18, which contains cavities 11 and 12 into which element 1 and element 2, respectively, of the strip can be inserted. One or more wedge shaped projections 17 on the sidewalls of chamber 18 serve to separate strip elements 1 and 2 as the strip is inserted into chamber 18. As the strip is inserted into chamber 18, element 1 first strikes the lower face of projection 17 and is forced down. This action in concert with the insertion action serves to further separate element 1 from element 2 to allow reliable insertion of element 2 into cavity 12.

A further wedge-shaped projection protrudes from the rear face of chamber 18. Conducting layers are mounted on the faces 13 and 14 of this projection, wherein the two conducting layers are electrically insulated from one another. These layers make electrical contact with the conducting coatings on strip elements 1 and 2. Electrically conducting wires or other conducting tracks 15 and 16 are electrically connected to the conducting layers on faces 13 and 14 and serve to make connection to the external circuitry. As one skilled in the art will appreciate, the device with surfaces comprising conducting layers 13 and 14 may be constructed so as to be integral with the projections 17.

Figure 11:
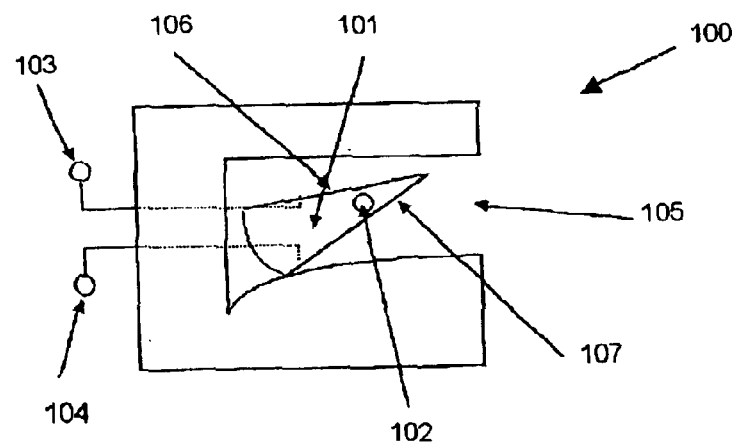
FIG. 11 provides a side view of an external circuit connector 100.
Figure 12:
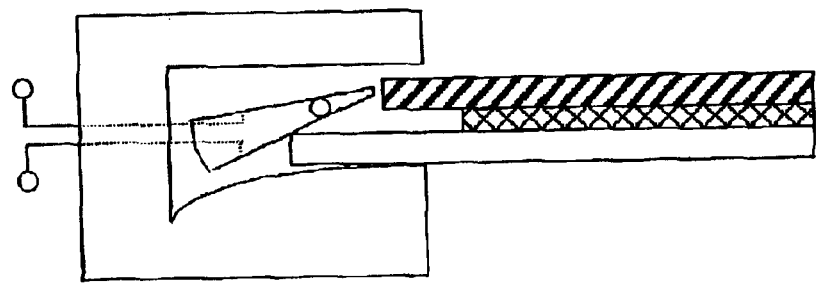
FIG. 12 provides an illustration depicting a strip partially inserted into an external circuit connector 100 as illustrated in FIG. 11.
Figure 13:
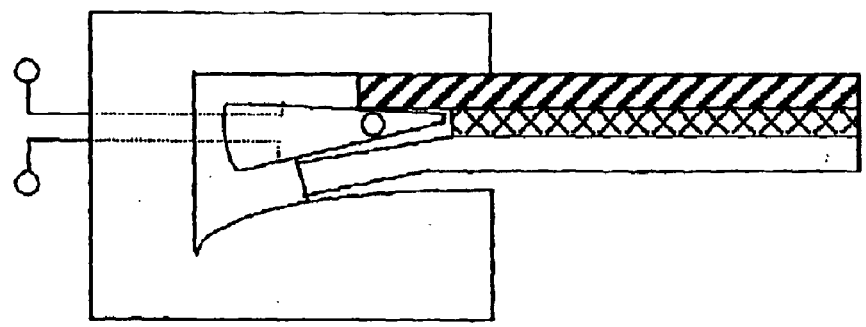
FIG. 13 provides an illustration depicting a strip fully inserted into an external circuit connector 100 as illustrated in FIG. 11.

A second embodiment is depicted in FIGS. 11 to 13. FIG. 11 shows a side view of the embodiment. FIGS. 12 and 13 show a side view of the embodiment with a strip partially or fully inserted respectively.

The external circuit connector 100, depicted in FIGS. 11 to 13, contains a chamber 105 which contains a wedge 101 that is able to rotate within the chamber 105 around the pivot point 102. The wedge comprises electrically conductive surfaces, 106 and 107 which are electrically connected to external connection points 103 and 104. In its initial position, the wedge 101 is held either by gravity or a spring tensioning device (not shown) such that it is positioned as shown in FIG. 11. When a strip is inserted into the chamber 105, the lower electrode element strikes the lower surface of wedge 101 behind the pivot point 102. This action rotates wedge 101 such that the point of the wedge 101 is positioned between the upper and lower electrode layers of the strip. Then, as the strip is further inserted into chamber 105, the upper wedge surface 106 is brought into contact with the conducting coating on the upper strip element. Electrical connection of the conducting coating on the upper strip element to connection point 103, via conducting surface 106 is then achieved, as is electrical connection of the conducting coating on the lower electrode strip element to connection point 104 via conducting surface 107.

The advantage of the embodiment shown in FIGS. 11 to 13 is that the point of the wedge 101 is automatically positioned between the upper and lower strip electrode elements to ensure reliable connection.

Electrochemical Cells

The electrochemical cell connectors of preferred embodiments are suitable for use in a variety of electrochemical cells. For example, the connectors may be used in conjunction with electrochemical cells used as amperometric sensors for the detection and quantification of analytes.

In such applications, the electrodes can be positioned such that the working electrode is isolated from the counter electrode reactions and reaction products, or positioned such that products of the counter electrode reaction diffuse to the working electrode where they react. The former type of electrochemical cell is well known in the prior art. The latter type of electrochemical cell is discussed in U.S. Pat. No. 6,179,979 and U.S. Pat. No. 5,942,102.

These two electrode configurations vary in that in the isolated case, the counter electrode is positioned far enough away from the working electrode such that during the time the cell is being used, products of electrochemical reactions at the counter electrode do not reach the working electrode. In practice, this is typically achieved by a separation of the working electrode from the counter electrode by at least a millimeter.

In the non-isolated configuration, the working electrode and the counter electrode are placed close enough together such that products of the electrochemical reactions at the counter electrode can diffuse to the working electrode during the time the cell is being used. These reaction products can then react at the working electrode, giving a higher current than may be present in the isolated electrode case. In the non-isolated configuration, the working electrode reactions can be described as coupled to the counter electrode reactions.

Fabricating the Electrochemical Cell

In certain embodiments, the electrochemical cells of preferred embodiments may be fabricated using methods similar to those disclosed in U.S. Pat. No. 5,942,102.

As will be recognized by one skilled in the art, the electrode layers and electrically insulating substrates may be independently selected as desired, for example, for ease of fabrication, for reducing materials costs, or to achieve other desirable attributes of the cell or fabrication process. Likewise, the electrode layers may be applied to the layers of electrically insulating substrates in any suitable pattern, for example, a pattern that only partially covers the substrate.

In preferred embodiments, various layers in the cell may be adhered using a suitable adhesive. Suitable adhesives include, for example, heat activated adhesives, pressure sensitive adhesives, heat cured adhesives, chemically cured adhesives, hot melt adhesives, hot flow adhesives, and the like. Pressure sensitive adhesives are preferred for use in certain embodiments where simplification of fabrication is desired. However, in other embodiments the tackiness of pressure sensitive adhesives may result in fabrication tool gumming or product tackiness. In such embodiments, heat or chemically cured adhesives are generally preferred. Especially preferred are the heat-activated and heat-cured adhesives, which can be conveniently activated at the appropriate time.

In certain embodiments, it may be preferred to use a hot melt adhesive. A hot melt adhesive is a solvent-free thermoplastic material that is solid at room temperature and is applied in molten form to a surface to which it adheres when cooled to a temperature below its melting point. Hot melt adhesives are available in a variety of chemistries over a range of melting points. The hot melt adhesive can be in the form of a web, nonwoven material, woven material, powder, solution, or any other suitable form. Polyester hot melt adhesives may be preferred for certain embodiments. Such adhesives (available, for example, from Bostik Corp. of Middleton, Mass.) are linear saturated polyester hot melts exhibiting melting points from 65° C. up to 220° C. and range from completely amorphous to highly crystalline in nature. Polyamide (nylon) hot melt adhesives, also available from Bostik, may also be preferred, including both dimer-acid and nylon-type polyamide adhesives. Suitable hot melt adhesive chemistries include EVA, polyethylene, and polypropylene.

Alternatively, in certain other embodiments it may be preferred to use lamination techniques to bond certain layers together. Suitable lamination techniques are described in application Ser. No. 09/694,106 filed Oct. 20, 2000 entitled "LAMINATES OF ASYMMETRIC MEMBRANES", now abandoned, and U.S. Pat. No. 6,596,112. The layers to be laminated are placed adjacent to each other and heat is applied, whereby a bond between the layers is formed. Pressure may also be applied to aid in forming the bond. Lamination methods may be preferred to bond any two materials capable of forming a bond under application of heat and/or pressure. Lamination is preferred to form a bond between two suitable polymeric materials.

Suitable electrically resistive materials which may be preferred as spacer layers, as supports for electrode layers, or in other layers in the cell, include, for example, materials such as polyesters, polystyrenes, polycarbonates, polyolefins, polyethylene terephthalate, glasses, ceramics, mixtures and/or combinations thereof, and the like. Examples of electrically resistive adhesives suitable for use as spacer or support layers include, but are not limited to, polyacrylates, polymethacrylates, polyurethanes, and sulfonated polyesters.

Chemicals for use in the cell, such as redox reagents, lysing agents, buffers, inert salts, and other substances, may be supported on the cell electrodes or walls, on one or more independent supports contained within cell, or may be self supporting. If the chemicals are to be supported on the cell electrodes or walls, the chemicals may be applied by use of application techniques well known in the art, such as ink jet printing, screen printing, lithography, ultrasonic spraying, slot coating, gravure printing, and the like. Suitable independent supports may include, but are not limited to, meshes, nonwoven sheets, fibrous fillers, macroporous membranes, and sintered powders. The chemicals for use in the cell may be supported on or contained within a support.

In a preferred embodiment, the preferred materials within the cell as well as the materials from which the cell is constructed are in a form amenable to mass production, and the cells themselves are designed for a single experiment then disposed of. A disposable cell is one that is inexpensive enough to produce that it is economically acceptable only for a single test. A disposable cell is one that may conveniently only be used for a single test, namely, steps such as washing and/or reloading of reagents may need to be taken to process the cell after a single use to render it suitable for a subsequent use.

Economically acceptable in this context means that the perceived value of the result of the test to the user is the same or greater than the cost of the cell to purchase and use, the cell purchase price being set by the cost of supplying the cell to the user plus an appropriate mark up. For many applications, cells having relatively low materials costs and simple fabrication processes are preferred. For example, the electrode materials of the cells may be inexpensive, such as carbon, or may be present in sufficiently small amounts such that expensive materials may be preferred. Screen printing carbon or silver ink is a process suitable for forming electrodes with relatively inexpensive materials. However, if it is desired to use electrode materials such as platinum, palladium, gold, or iridium, methods with better material utilization, such as sputtering or evaporative vapor coating, are preferred as they may yield extremely thin films. The substrate materials for the disposable cells are also preferably inexpensive. Examples of such inexpensive materials are polymers such as polyvinylchloride, polyimide, polyester and coated papers and cardboard.

Cell assembly methods are preferably amenable to mass production. These methods include fabricating multiple cells on cards and separating the card into individual strips subsequent to the main assembly steps, and web fabrication where the cells are produced on a continuous web, which is subsequently separated into individual strips. Card processes are most suitable when close spatial registration of multiple features is desired for the fabrication and/or when stiff cell substrate materials are preferred. Web processes are most suitable when the down web registration of features is not as critical and flexible webs may be preferred.

In certain embodiments, a convenient single use for the electrochemical cell may be desirable so that users are not tempted to try to reuse the cell and possibly obtain an inaccurate test result. Single use of the cell may be stated in user instructions accompanying the cell. More preferably, in certain embodiments where a single use is desirable the cell may be fabricated such that using the cell more than once is difficult or not possible. This may be accomplished, for example, by including reagents that are washed away or consumed during the first test and so are not functional in a second test. Alternatively, the signal of the test may be examined for indications that reagents in the cell have already reacted, such as an abnormally high initial signal, and the test aborted. Another method includes providing a means for breaking electrical connections in the cell after the first test in a cell has been completed.

The Electrodes

In a preferred embodiment wherein the electrochemical cell detects the presence and/or amount of analyte in the sample, or a substance indicative of the presence and/or amount of analyte present in the sample, at least one of the electrodes in the cell is a working electrode. When the potential of the working electrode is indicative of the level of analyte (such as in a potentiometric sensor) a second electrode acting as reference electrode is present which acts to provide a reference potential.

In the case of an amperometric sensor wherein the working electrode current is indicative of the level of an analyte, such as glucose, at least one other electrode is preferably present which functions as a counter electrode to complete the electrical circuit. This second electrode may also function as a reference electrode. Alternatively, a separate electrode may perform the function of a reference electrode.

Materials suitable for the working, counter, and reference electrodes are compatible with any reagents or substances present in the device. Compatible materials do not substantially react chemically with other substances present in the cell. Examples of such suitable materials may include, but are not limited to, carbon, carbon and an organic binder, platinum, palladium, carbon, indium oxide, tin oxide, mixed indium/tin oxides, gold, silver, iridium, and mixtures thereof. These materials may be formed into electrode structures by any suitable method, for example, by sputtering, vapor coating, screen printing, thermal evaporation, gravure printing, slot coating or lithography. In preferred embodiments, the material is sputtered or screen-printed to form the electrode structures.

Non-limiting examples of materials preferred for use in reference electrodes include metal/metal salt systems such as silver in contact with silver chloride, silver bromide or silver iodide, and mercury in contact mercurous chloride or mercurous sulfate. The metal may be deposited by any suitable method and then brought into contact with the appropriate metal salt. Suitable methods include, for example, electrolysis in a suitable salt solution or chemical oxidation. Such metal/metal salt systems provide better potential control in potentiometric measurement methods than do single metal component systems. In a preferred embodiment, the metal/metal salt electrode systems are preferred as a separate reference electrode in an amperometric sensor.

Any suitable electrode spacing may be used. In certain embodiments it may be preferred that the electrodes be separated by a distance of about 500 $\mu$m, 400 $\mu$m, 300 $\mu$m, 200 $\mu$m, 100 $\mu$m, 50 $\mu$m, 200 $\mu$m, 10 $\mu$m, or less. In other embodiments it may be preferred that the electrodes be separated by a distance of about 500 $\mu$m, 600 $\mu$m, 700 $\mu$m, 800 $\mu$m, 900 $\mu$m, 1 mm, or more.

Lysing Agents

In certain embodiments, it may be desired to include one or more lysing agents in the electrochemical cell. Suitable lysing agents include detergents, both ionic and non-ionic, proteolytic enzymes, and lipases. Suitable ionic detergents include, for example, sodium dodecyl sulfate and cetyl trimethylammonium bromide. Non-limiting examples of proteolytic enzymes include trypsin, chymotrypsin, pepsin, papain, and Pronase E, a very active enzyme having broad specificity. Nonionic surfactants suitable for use include, for example, ethoxylated octylphenols, including the TRITON X™ Series available from Rohm & Haas of Philadelphia, Pa. In a preferred embodiment, saponins, namely, plant glycosides that foam in water, are preferred as the lysing agent. In a particularly preferred embodiment, alkali metal salts of deoxycholic acid, available from Sigma Aldrich Pty. Ltd. of Castle Hill, NSW, Australia, are preferred as lysing agents.

Redox Reagent

Redox reagents may also be included in the electrochemical cell in preferred embodiments. Preferred redox reagents for use in electrochemical cells for measuring glucose in blood include those which are capable of oxidizing the reduced form of enzymes that are capable of selectively oxidizing glucose. Examples of suitable enzymes include, but are not limited to, glucose oxidase dehydrogenase, PQQ dependent glucose dehydrogenase, and NAD dependent glucose dehydrogenase. Examples of redox reagents suitable for use in analyzing glucose include, but are not limited, to salts of ferricyanide, dichromate, vanadium oxides, permanganate, and electroactive organometallic complexes. Organic redox reagents such as dichlorophenolindophenol, and quinones are also suitable. In a preferred embodiment, the redox reagent for analyzing glucose is ferricyanide.

Buffers

Optionally, a buffer may be present along with a redox reagent in dried form in the electrochemical cell. If a buffer is present, it is present in an amount such that the resulting pH level is suitable for adjusting the oxidizing potential of the redox reagent to a level suitable for oxidizing, for example, glucose but not other species that it is not desired to detect. The buffer is present in a sufficient amount so as to substantially maintain the pH of the sample at the desired level during the test. Examples of suitable buffers include phosphates, carbonates, alkali metal salts of mellitic acid, alkali metal salts of citric acid, and alkali metal salts of citraconic acid. The choice of buffer may depend, amongst other factors, on the desired pH. The buffer is selected so as not to react with the redox reagent.

Inert Salts

Inert salts preferred for use in various embodiments include salts that dissociate to form ions in the sample to be analyzed, but do not react with any of the redox reagents or other substances in the sample or in the cell, including with the cell electrodes. Examples of suitable inert salts include, but are not limited to, alkali metal chlorides, nitrates, sulfates, and phosphates.

Other Substances Present Within the Cell

In addition to redox reagents and buffers, other substances may also be present within the electrochemical cell. Such substances include, for example, viscosity enhancers and low molecular weight polymers. Hydrophilic substances may also be contained within the cell, such as polyethylene glycol, polyacrylic acid, dextran, and surfactants such as those marketed by Rohm & Haas Company of Philadelphia, Pa., under the trade name TRITON™ or by ICI Americas Inc. of Wilmington, Del., under the trade name TWEEN™. In a preferred embodiment Pluronic surfactants and anti-foaming agents available from BASF are present. Such substances may enhance the fill rate of the cell, provide a more stable measurement, and inhibit evaporation in small volume samples.

Electrical Circuit

The electrically conductive layers are preferably connected via the connectors described herein to electrical circuits capable of applying potentials between the electrodes and measuring the resulting currents, for example, meters. Suitable meters may include one or more of a power source, circuitry for applying controlled potentials or currents, a microprocessor control device, computer, or data storage device, a display device, an audible alarm device, or other devices or components as are known in the art. The meter may also be capable of being interfaced to a computer or data storage device. For example, a typical meter may be a hand-held device that is powered by a battery, controlled by an on-board microprocessor, and contains circuitry for applying predetermined potentials or currents between, for example, strip electrode connection pins and circuitry such as an analog-to-digital converter. In this embodiment, the analog signal from the strip may be converted to a digital signal that can be analyzed and/or stored by a microprocessor. The meter may also contain a display such as a Liquid Crystal Display and suitable associated circuitry to display the result of the test to the user. In an alternative embodiment, the meter may incorporate specialized circuitry, such as potential application and signal acquisition circuitry. Such specialized circuitry may be incorporated in a separate module that may be interfaced with a generic computing device, such as a hand-held computer or other type of computer. In such an embodiment, the generic device may perform the control, analysis, data storage, and/or display functions. Such an embodiment allows for a less expensive meter to be produced because the generic computing device may be preferred for many functions and as such is not considered as part of the cost of the electrochemical measurement system. In either of these meter embodiments, the meter or generic computing device may be capable of communication with external devices such as local computer networks or the Internet to facilitate the distribution of test results and the provision of system upgrades to the user.

The above description provides several methods and materials of the present invention. This invention is susceptible to modifications in the methods and materials, as well as alterations in the fabrication methods and equipment. Such modifications will become apparent to those skilled in the art from a consideration of this disclosure or practice of the invention provided herein. Consequently, it is not intended that this invention be limited to the specific embodiments provided herein, but that it cover all modifications and alternatives coming within the true scope and spirit of the invention as embodied in the attached claims. All references cited herein are hereby incorporated by reference in their entireties.

What is claimed is:

1. A method for forming an electrical connection between an electrochemical cell and a meter, the method comprising the steps of:
    a) providing an electrochemical cell, the electrochemical cell comprising a first insulating substrate carrying a first electrically conductive coating, a second insulating substrate carrying a second electrically conductive coating, and an insulating spacer layer disposed therebetween, the electrically conductive coatings being disposed to face each other in a spaced apart relationship, wherein an edge of the first insulating substrate carrying the first electrically conductive coating extends beyond an edge of the second insulating substrate carrying the second electrically conductive coating and beyond an edge of the insulating spacer layer, and wherein the edge of the second insulating substrate carrying the second electrically conductive coating extends beyond the edge of the insulating spacer layer;
    b) providing a meter, the meter comprising a wedge, the wedge comprising an upper wedge conductive surface and a lower wedge conductive surface, the conductive surfaces in electrical communication with the meter; and
    c) inserting a portion of the electrochemical cell into the meter, whereby the wedge is inserted between the portion of the first insulating substrate carrying the first electrically conductive coating and the portion of the second insulating substrate carrying the second electrically conductive coating that extends beyond the edge of the insulating spacer layer, whereby an electrical connection between the first electrically conductive coating and the lower wedge conductive surface is formed, and whereby an electrical connection between the second electrically conductive coating and the upper wedge conductive surface is formed.

2. The method of claim 1, the meter further comprising a pivot point, wherein the wedge is capable of rotating on the pivot point.

* * * * *